United States Patent [19]

Biedermann et al.

[11] 4,086,283

[45] Apr. 25, 1978

[54] PROCESS FOR PREPARING THYMOL

[75] Inventors: Wolfgang Biedermann; Horst Köller, both of Krefeld; Karlfried Wedemeyer, Cologne, all of Germany

[73] Assignee: Bayer Aktiengesellschaft, Leverkusen, Germany

[21] Appl. No.: 692,170

[22] Filed: Jun. 2, 1976

[30] Foreign Application Priority Data

Jun. 25, 1975 Germany .............................. 2528303

[51] Int. Cl.² .............................................. C07C 39/06
[52] U.S. Cl. ............................. 260/626 T; 260/624 R
[58] Field of Search ........... 260/624 R, 626 T, 626 R, 260/624

[56] References Cited

U.S. PATENT DOCUMENTS

| | | | |
|---|---|---|---|
| 1,886,311 | 11/1932 | Skraup et al. | 260/626 T |
| 1,902,904 | 3/1933 | Schollkupe et al. | 260/626 T |
| 3,968,173 | 7/1976 | Klein et al. | 260/626 T |

*Primary Examiner*—James O. Thomas, Jr.
*Assistant Examiner*—Werren B. Lone
*Attorney, Agent, or Firm*—Burgess, Dinklage & Sprung

[57] ABSTRACT

Thymol can be prepared on a continuous basis by reacting m-cresol with propylene and/or compounds which eliminate propylene, over aluminum oxide catalysts in the presence of a nitrogen base. The aluminum oxide catalyst is an active or activated hydrated aluminum oxide having a particle size between 0.5 and 20 mm, a BET surface area of at least 200 m²/g, a porosity equal to or greater than 0.5 mm/g, a boehmite content of 5 to 40 percent by weight, and an X-ray spectrum which shows the reflections of γ-alumina wherein the content of microcrystalline constituents is less than 50 percent by weight.

5 Claims, No Drawings

PROCESS FOR PREPARING THYMOL

BACKGROUND

This invention relates to a continuous process for the preparation of thymol by propylation of m-cresol with propylene.

It is already known to prepare thymol by reaction of m-cresol with propylene or compounds which eliminate propylene, such as oligomers of propylene, isopropanol, thymol isomers or poly-propylated m-cresol.

These alkylation reactions are carried out at temperatures of up to about 400° C, under atmospheric pressure or, preferably, under a pressure of up to about 100 bars, and in the presence of catalysts. Examples of catalysts employed are catalysts of the Friedel-Craffts type, metal salts, aqueous solutions of metal salts, aluminium oxides, aluminium oxides pretreated with metal sulphates, natural and synthetic activated clays, alumosilicates, molecular sieves, treated natural products, such as bleaching earths, and cresolates (see, for example, East German Pat. No. 36,644, (German Published Specifications 1,815,846 and 2,139,622 and Angew. Chemie 1957, page 702).

However, these known processes suffer from the following serious disadvantages:

They can only be carried out discontinuously and/or require long reaction times; the catalysts used have too short a life. Or the catalysts require regenerating; the catalysts are difficult to separate off; the purity of the m-cresol to be employed has to conform to high standards (for example, the cresol must be dry).

Furthermore, the isolation of the pure thymol from the crude thymols obtained in the known processes presents very particular difficulties. The crude thymols obtained from the propylation of m-cresol in general contain 55 to 60 percent by weight of thymol, 25 to 30 percent by weight of unreacted m-cresol and 10 to 20 percent by weight of by-products. A decisive factor regarding the isolation of thymol from this crude thymol is the composition of the by-products. If these consist of compounds which can easily be separated from thymol, the isolation of the thymol presents no difficulties. If, on the other hand, the by-products contain compounds which hardly differ from thymol in their physical properties, especially their boiling point, for example 2-isopropyl-4-methyl-phenol, the preparation of the thymol in a pure form is, if not impossible, at least very expensive. 2,4-Diisopropyl-5-methyl-phenol is also an undesired by-product, since, when it is re-used as a propylating agent, it only reacts sluggishly.

SUMMARY

It has now been found, surprisingly, that the above-mentioned disadvantages of the known processes for the preparation of thymol can be overcome by carrying out the reaction of m-cresol with propylene and/or compounds which eliminate propylene over aluminium oxide catalysts in the presence of a catalytic amount of a nitrogen base.

The invention therefore relates to a continuous process for the preparation of thymol by reaction of m-cresol with propylene and/or compounds which eliminate propylene, which is characterised in that the reaction is carried out over aluminium oxide catalysts in the presence of a nitrogen base.

DESCRIPTION

The process according to the invention is distinguished by the fact that it yields, even in the presence of small amounts of water in the m-cresol, and independently of the starting material, that is to say independently of whether m-cresol and propylene, or by-products arising in working up crude thymol, are employed, a crude thymol of constant composition and quality, from which thymol in a purity of over 99.5% can be isolated without difficulties, and the by-products of which can always be recycled to the reaction. In the process according to the invention, the activity of the catalyst also remains preserved for very long periods.

The nitrogen bases to be used according to the invention are preferably ammonia and its basic, that is to say salt-forming substitution products. As examples of basic substitution products there may be mentioned: hydrazine, aliphatic amines such as methylamine, dimethylamine, ethylamine, 2-hydroxyethylamine, propylamine and butylamine, cycloaliphatic amines, such as cyclohexylamine and dicyclohexylamine, araliphatic amines, such as benzylamine, aromatic amines, such as aniline and dimethylaniline, heterocyclic amines, such as pyridine and piperidine, and basic acid amides, such as urea.

The nitrogen bases are generally added to the m-cresol. However, when using certain nitrogen bases, for example ethanolamine, it is also possible to charge the catalyst with these. These special amines are held so firmly by the catalyst that they are virtually not carried away by the product stream. Supplementing the amine on the catalyst is only necessary at fairly long intervals of time. The catalyst can be charged with the amine by, for example, first passing a volume, equal to several times the reactor volume, of the reaction mixture, containing the particular nitrogen base, through the catalyst. The addition of amine to the reaction mixture can then be discontinued, since the catalyst has then been brought, by means of the base, to the condition for optimum reaction.

The nitrogen bases are added to the cresol in an amount such that the content of basic nitrogen in the cresol is 10 to 1,000 ppm, preferably 100 to 500 ppm. Should the basic nitrogen in the cresol, on repeated recycling from the crude thymol distillate, have accumulated to the point that its content has increased to values greater than 1,000 ppm, it is advisable to lower this content of basic nitrogen either by suitable purification operations or by mixing the nitrogen-containing cresol with nitrogen-free cresol before it is recycled to the reaction.

Suitable aluminium oxide catalysts for the process according to the invention have above all proved to be active or activated hydrated aluminium oxides, the particle size of which is between 0.5 and 20 mm, preferably 2 to 10 mm, the BET surface area of which is at least 200 m$^2$/g, preferably more than 300 m$^2$/g, the porosity of which is equal to, or greater than, 0.5 ml/g, the boehmite content of which is 5 to 40 percent by weight, and the X-ray spectra of which show the reflections of γ-alumina, in which the content of microcrystalline constituents is less than 50 percent by weight. Such aluminium oxide catalysts are described, for example, in British Pat. Nos. 1,367,925 and 1,404,543.

The process according to the invention is in general carried out at pressures of up to about 100 bars, preferably 50 to 60 bars, and at temperatures of 200° to 400° C, preferably 280° to 380° C.

The starting compounds employed are propylene or compounds which eliminate propylene, such as thymol isomers, propylene oligomers and poly-propylated cresols. The m-cresol used should preferably be of about 98.5% purity, having o-cresol should be less than 0.5 percent by weight, its content of p-cresol less than 1.5 percent by weight and its content of water less than 0.1 percent by weight. Other impurities, such as phenols, xylenols and the like, should not exceed a total of 0.2 percent by weight; the content of basic nitrogen should be less than 1,000 ppm.

The process according to the invention is in general carried out by bringing the content of basic nitrogen in the cresol to the desired value, then mixing the cresol with propylene or compounds which eliminate propylene, introducing the mixture into the reactor, containing the catalyst, from the bottom, and taking off, at the top of the reactor, the crude thymol formed. The crude thymol is subsequently worked up, preferably by distillation. The by-products obtained on working up are returned into the reaction circulation together with the recovered cresol, if appropriate after addition of fresh cresol and/or propylene and, if appropriate, after addition of nitrogen bases.

An essential advantage of the process according to the invention is that it produces no enrichment in by-products and that it also does not form interfering by-products, which have to be expelled from the reaction circulation; instead, the by-products can always be directly returned to the reaction.

Notes on the Examples

The symbols and figures used in the Examples and Tables in order to characterise the compounds have the following meaning:

1 = m-cresol
2 = 2-isopropyl-3-methyl-phenol (vic. thymol)
3 = 2-isopropyl-4-methyl-phenol
4 = 2-isopropyl-5-methyl-phenol (thymol)
5 = 3-isopropyl-5-methyl-phenol (isothymol)
6 = 4-isopropyl-5-methyl-phenol (p-thymol)
7 = 2,4-diisopropyl-5-methyl-phenol
8 = 2,6-diisopropyl-5-methyl-phenol
$\Sigma$ = sum of the by-products, that is to say sum of the products 2, 3, 5, 6, 7 and 8.

The m-cresol ("fresh cresol") used in the Examples had the following composition: 98.6 percent by weight of m-cresol, 0.03 percent by weight of o-cresol, 1.2 percent by weight of p-cresol, 0.06 percent by weight of unknown compounds and 0.05 percent by weight of water.

The propylene used in the Examples had the following composition: 98.2 percent by weight of propylene and 1.8 percent by weight of propane.

The crude thymols obtained were analysed by gas chromatography. The percentage data are percentages by weight.

EXAMPLE 1

Reactor used: 12 m length, 500 mm internal width; amount of catalyst: 2 m$^3$; catalyst: active alumina (particle size: 2 to 5 mm; BET surface area: 325 m$^2$/g; porosity: 0.6 ml/g; boehmite content: 35 percent by weight; micro-crystalline content: 40 percent by weight).

Per hour, 300 l of liquid cresol and 250 l of liquid propylene are pumped through the reactor, which is pre-warmed to 300° C (the reactants are introduced into the reactor at the bottom and the crude thymol is taken off at the top of the reactor). Reaction temperature 360° to 365° C; pressure: 48 to 50 bars. Yield: 10.3 tonnes of crude thymol/day.

The following m-cresols are reacted with propylene in this way:

| Cresol | Content of basic N[ppm] |
| --- | --- |
| A | 5 |
| A 1 | 400 |
| B | 150 |
| B 1 | 400 |
| C | 300 |
| C 1 | 400 |

The content of 400 ppm of basic nitrogen in cresols A 1, B 1 and C 1 was obtained by adding 2,350 mg of cyclohexylamine/l of cresol A, 1,450 mg of cyclohexylamine/l of cresol B and 580 mg of cyclohexylamine/l of cresol C.

According to analysis by gas chromatography, the crude thymols obtained from the various cresols had the composition shown in Table 1 (the figures shown denote percentages by weight):

Table 1

| Cresol | Compound | | | | | | | | |
| --- | --- | --- | --- | --- | --- | --- | --- | --- | --- |
| | 1 | 2 | 3 | 4 | 5 | 6 | 7 | 8 | $\Sigma$ |
| A | 17.7 | 1.6 | 0.5 | 61.4 | 3.4 | 3.2 | 8.1 | 2.9 | 19.70 |
| A 1 | 24.7 | 2.5 | 0.06 | 61.5 | 1.1 | 1.8 | 4.8 | 2.6 | 12.86 |
| | | | | | | | | $\Delta\Sigma=$ | 6.84 |
| B | 21.5 | 2.0 | 0.2 | 61.5 | 2.0 | 2.4 | 6.5 | 2.6 | 15.70 |
| B 1 | 24.5 | 2.5 | 0.04 | 61.0 | 1.1 | 1.6 | 5.1 | 2.6 | 12.94 |
| | | | | | | | | $\Delta\Sigma=$ | 2.87 |
| C | 25.0 | 2.5 | 0.2 | 61.2 | 1.1 | 2.1 | 4.4 | 2.4 | 12.70 |
| C 1 | 26.0 | 2.9 | 0.04 | 61.0 | 0.8 | 2.0 | 3.8 | 2.3 | 11.84 |
| | | | | | | | | $\Delta\Sigma=$ | 0.86 |

It follows from Table 1 that:
(1) The sum of the by-products formed ($\Sigma$) decreases with increasing nitrogen content of the m-cresol employed.
(2) The decrease in the content of by-products is associated with an increase in the cresol content; the thymol content remains practically unchanged.
(3) The content of the particularly objectionable impurity 3 in the crude thymol is lowered decisively (to about 1/5).

EXAMPLE 2

The procedure followed was as described in Example 1, except that in place of the cresols used there, a mixture (D) of "recycled cresol" (obtained on working up crude thymol by distillation) and fresh cresol (content of basic nitrogen: 5 ppm) or a mixture of "recycled cresol" and fresh cresol, of which the content of basic nitrogen had been adjusted to 400 ppm by adding cyclohexylamine (mixture D 1) was used, and instead of 300 l of cresol and 250 l of propylene, 150 l of recycled cresol + 170 l of fresh cresol and 140 l of propylene were pumped hourly through the reactor.

The recycled cresol and the mixture of recycled cresol + fresh cresol used for the propylation had the following composition:

| Compound | Recycled cresol | Mixture |
| --- | --- | --- |
| 1 | 60.8% | 77.8% |
| 2 | 4.5% | 3.8% |
| 3 | 0.9% | 0.4% |
| 4 | 12.8% | 2.9% |
| 5 | 3.1% | 6.8% |
| 6 | 4.1% | 1.4% |

-continued

| Compound | Recycled cresol | Mixture |
| --- | --- | --- |
| 7 | 4.8% | 2.3% |
| 8 | 7.7% | 2.2% |
| Σ | 25.1% | 13.0% |

According to analysis by gas chromatography, the crude thymols obtained from the various cresol mixtures D and D 1 had the composition shown in Table 2 (the figures shown denote percentages by weight):

Table 2

| Cresol | Compound | | | | | | | | |
| --- | --- | --- | --- | --- | --- | --- | --- | --- | --- |
| | 1 | 2 | 3 | 4 | 5 | 6 | 7 | 8 | Σ |
| D | 23.1 | 2.3 | 0.8 | 58.1 | 2.4 | 2.0 | 5.1 | 3.9 | 16.5 |
| D 1 | 26.5 | 2.4 | 0.04 | 57.5 | 1.7 | 1.4 | 4.3 | 3.7 | 13.54 |

It follows from the data shown in Table 2 that the cresol mixture D gives a crude thymol wherein the content of by-products is 3.5 percent by weight higher than the content of the starting mixture D, whilst the content of by-products of the crude thymol obtained from the cresol mixture D 1 has only increased by 0.5 percent by weight.

EXAMPLE 3

The procedure followed was as described in Example 2, with the sole difference that the "recycled cresol" used was a cresol which had been obtained on working up, by distillation, a crude thymol manufactured in the presence of added base. (E = mixture of "recycled cresol" and fresh cresol; E 1 = mixture E, adjusted with cyclohexylamine to a basic nitrogen content of 400 ppm).

The recycled cresol and the mixture of recycled cresol and fresh cresol used for the propylation had the following composition:

| Compound | Recycled cresol | Mixture |
| --- | --- | --- |
| 1 | 61.4% | 78.2% |
| 2 | 4.8% | 2.8% |
| 3 | 0.1% | 0.06% |
| 4 | 13.1% | 6.9% |
| 5 | 2.9% | 1.9% |
| 6 | 4.8% | 2.2% |
| 7 | 4.5% | 2.4% |
| 8 | 7.3% | 3.5% |
| Σ | 24.4% | 12.86% |

According to analysis by gas chromatography, the crude thymols obtained from the various cresol mixtures E and E 1 had the composition shown in Table 3 (the figures shown denote percentages by weight):

Table 3

| Cresol | Compound | | | | | | | | |
| --- | --- | --- | --- | --- | --- | --- | --- | --- | --- |
| | 1 | 2 | 3 | 4 | 5 | 6 | 7 | 8 | Σ |
| E | 25.9 | 2.8 | 0.05 | 59.1 | 1.8 | 1.6 | 4.7 | 2.9 | 13.25 |
| E 1 | 26.8 | 3.2 | 0.03 | 58.8 | 1.7 | 1.6 | 3.7 | 2.7 | 12.93 |

A comparison of the amounts of by-products (Σ) in the starting mixture and in the crude thymols obtained therefrom, shows that in the case of E the by-products increase by 0.4 percent by weight whilst the amount of by-products in the crude thymol produced from E 1 remains practically unchanged.

EXAMPLE 4

The procedure followed was as described in Example 3, with the sole difference that the "recycled cresol" used was a cresol which had been obtained on working up the crude thymol prepared from E 1. The recycled cresol and the mixture of recycled cresol and fresh cresol used for the propylation had the following composition:

| Compound | Recycled cresol | Mixture |
| --- | --- | --- |
| 1 | 61.8% | 78.4% |
| 2 | 4.7% | 2.7% |
| 3 | 0.1% | 0.05% |
| 4 | 12.9% | 6.8% |
| 5 | 2.8% | 1.7% |
| 6 | 4.6% | 2.5% |
| 7 | 4.6% | 2.2% |
| 8 | 7.1% | 3.5% |
| Σ | 22.9% | 12.65% |

For the propylation, the content of basic nitrogen in the mixture of recycled cresol and fresh cresol was adjusted to 400 ppm by adding cyclohexylamine. According to analysis by gas chromatography, the crude thymol obtained had the following composition:

| | |
| --- | --- |
| 1 | 26.4% |
| 2 | 3.1% |
| 3 | 0.02% |
| 4 | 58.2% |
| 5 | 1.6% |
| 6 | 1.8% |
| 7 | 3.4% |
| 8 | 2.8% |
| Σ | 12.72% |

It follows from the composition of the crude thymol that the sum of the by-products in the crude thymol remains practically constant during proylation, that is to say that on maintaining the content, according to the invention, of basic nitrogen in the cresol employed for the propylation, the cresol can be recycled without leading to an accumulation of by-products in the crude thymol.

EXAMPLE 5

Reactor used: 2 m length, 90 mm internal width; amount of catalyst: 12.2 l; catalyst: see Example 1.

Per hour, 1.8 l of liquid cresol and 1.5 l of liquid propylene are pumped into the reactor heated to 300° C by means of preheated nitrogen (the reactants being introduced into the reactor from the bottom and the crude thymol being taken off at the top of the reactor). Reaction temperature: 360° C; pressure: 50 bars.

Propylene was reacted with the following m-cresols in this manner:
   (a) m-Cresol, basic nitrogen content: 400 ppm, set up by addition of ammonia.
   (b) m-Cresol, basic nitrogen content: 400 ppm, set up by addition of urea.
   (c) m-Cresol, basic nitrogen content: 400 ppm, set up by addition of pyridine.
   (d) m-Cresol, basic nitrogen content: 400 ppm, set up by addition of 2-hydroxyethylamine.

According to analysis by gas chromatography, the crude thymols obtained from the various cresols (a), (b), (c) and (d) had the composition shown in Table 4 (the figures shown denote percentages by weight).

Table 4

| Cresol | Compound | | | | | | | | |
| --- | --- | --- | --- | --- | --- | --- | --- | --- | --- |
| | 1 | 2 | 3 | 4 | 5 | 6 | 7 | 8 | Σ |
| a) | 25.2 | 2.1 | 0.02 | 60.5 | 1.8 | 2.7 | 4.1 | 2.0 | 12.72 |
| b) | 24.9 | 2.8 | 0.05 | 60.8 | 2.0 | 2.3 | 3.9 | 1.9 | 12.95 |

Table 4-continued

| Cresol | Compound | | | | | | | | |
|---|---|---|---|---|---|---|---|---|---|
| | 1 | 2 | 3 | 4 | 5 | 6 | 7 | 8 | Σ |
| c) | 27.0 | 2.6 | 0.06 | 59.2 | 2.1 | 2.4 | 3.8 | 1.7 | 12.66 |
| d) | 24.4 | 2.4 | 0.04 | 60.8 | 1.7 | 2.9 | 4.0 | 2.1 | 12.14 |

What is claimed is:

1. In a process for the preparation of thymol by reacting m-cresol with propylene and/or compounds which eliminate propylene in the presence of an aluminum oxide catalyst the improvement comprising carrying out said process continuously and this in the presence of 10 to 1000 ppm of a nitrogen base selected from the group consisting of ammonia, hydrazine, alkyl, dialkyl or hydroxyalkyl amines having up to four carbon atoms in the alkyl group, cycloalkyl amines having 6–12 carbon atoms, benzylamine, aniline, dimethylaniline, pyridine, piperidine, and urea at temperatures of 200° to 400° C and at pressures up to about 100 bars.

2. Process of claim 1 wherein the nitrogen base is admixed with the m-cresol or adsorbed on the catalyst.

3. Process of claim 1 wherein the nitrogen base is added to the m-cresol in an amount of 10 to 1,000 ppm.

4. Process of claim 1 wherein the nitrogen base is added to the m-cresol in an amount of 100 to 500 ppm.

5. Process of claim 1 wherein the aluminum oxide catalyst used is an active or activated hydrated aluminum oxide, having a particle size between 0.5 and 20 mm, a BET surface area of at least 200 m$^2$/g, a porosity equal to or greater than, 0.5 mm/g, a boehmite content of 5 to 40 percent by weight, and an X-ray spectrum of which shows the reflections of γ-alumina wherein the content of micro-crystalline constitutuents is less than 50 percent by weight.

* * * * *